US012618816B2

(12) United States Patent
Steiner et al.

(10) Patent No.: US 12,618,816 B2
(45) Date of Patent: May 5, 2026

(54) GAS CONCENTRATION SENSOR AND SENSOR CALIBRATION WITHOUT USE OF A TARGET GAS

(71) Applicant: Infineon Technologies AG, Neubiberg (DE)

(72) Inventors: Christoph Steiner, St. Margarethen a. d. Raab (AT); Matthias Eberl, Taufkirchen (DE); Johannes Hufnagl, Graz (AT)

(73) Assignee: Infineon Technologies AG, Neubiberg (DE)

( * ) Notice: Subject to any disclaimer, the term of this patent is extended or adjusted under 35 U.S.C. 154(b) by 358 days.

(21) Appl. No.: 18/460,801

(22) Filed: Sep. 5, 2023

(65) Prior Publication Data

US 2025/0076266 A1    Mar. 6, 2025

(51) Int. Cl.
*G01N 33/00*      (2006.01)
*G01N 25/18*      (2006.01)

(52) U.S. Cl.
CPC ......... *G01N 33/0006* (2013.01); *G01N 25/18* (2013.01)

(58) Field of Classification Search
CPC ..... G01N 30/66; G01N 33/0006; G01N 25/18
USPC ........... 73/1.01–1.3, 1.06, 25.01, 25.3, 25.05
See application file for complete search history.

(56) References Cited

U.S. PATENT DOCUMENTS

2006/0042351 A1*   3/2006   Liu .................... G01N 27/4163
                                                       73/1.06

FOREIGN PATENT DOCUMENTS

JP          2016042054 A *   3/2016  ............. G01N 25/18

* cited by examiner

*Primary Examiner* — Laura Martin
*Assistant Examiner* — Anthony W Megna Fuentes
(74) *Attorney, Agent, or Firm* — Harrity & Harrity, LLP

(57) ABSTRACT

A sensor calibration system includes a gas sensor configured to measure a thermal conductivity of a target gas. The gas sensor includes a reference chamber containing a reference gas, a measurement chamber containing a measurement gas, and a calibration circuit. The reference gas has a first thermal conductivity profile and the measurement gas has a, different, second thermal conductivity profile that are dependent on a first environmental stimulus and a second environmental stimulus. The calibration circuit is configured to, while the first environmental stimulus is varied and the second environmental stimulus is fixed, acquire a plurality of measurements. Each measurement of the plurality of measurements is representative of a difference in thermal conductivity between thermal conductivities of the reference gas and the measurement gas. The calibration circuit is configured to determine a target gas sensitivity of the gas sensor to the target gas based on the plurality of measurements.

17 Claims, 3 Drawing Sheets

100

200

300

302 304

308

306

400

410

Controller

T P TG

402

Vin

404

Gas sensor

406

Gas sensor

408

Gas sensor

412

Vout

Measurement circuit

Processor

414

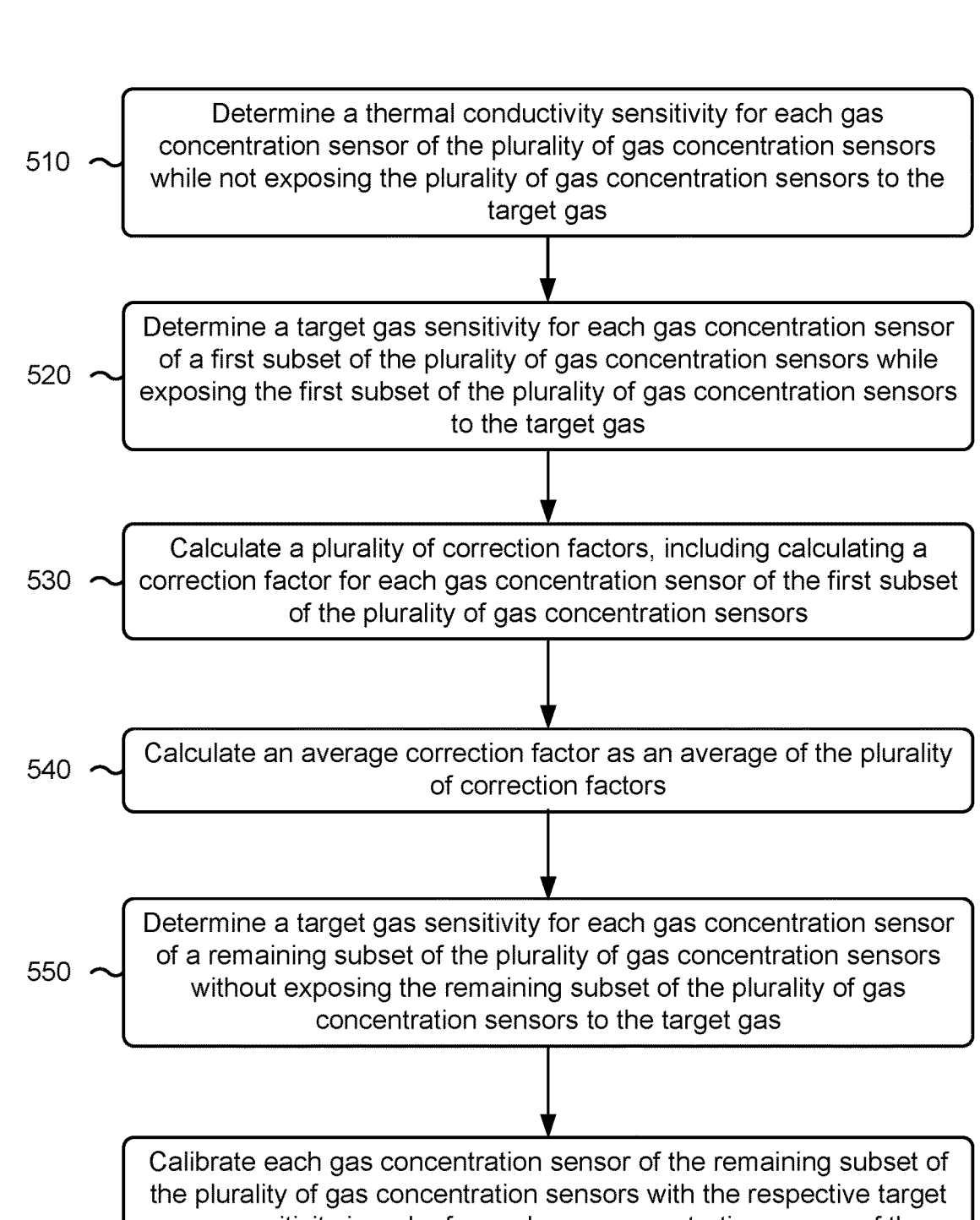

500

510 — Determine a thermal conductivity sensitivity for each gas concentration sensor of the plurality of gas concentration sensors while not exposing the plurality of gas concentration sensors to the target gas 520 — Determine a target gas sensitivity for each gas concentration sensor of a first subset of the plurality of gas concentration sensors while exposing the first subset of the plurality of gas concentration sensors to the target gas 530 — Calculate a plurality of correction factors, including calculating a correction factor for each gas concentration sensor of the first subset of the plurality of gas concentration sensors 540 — Calculate an average correction factor as an average of the plurality of correction factors 550 — Determine a target gas sensitivity for each gas concentration sensor of a remaining subset of the plurality of gas concentration sensors without exposing the remaining subset of the plurality of gas concentration sensors to the target gas 560 — Calibrate each gas concentration sensor of the remaining subset of the plurality of gas concentration sensors with the respective target gas sensitivity in order for each gas concentration sensor of the remaining subset of the plurality of gas concentration sensors to perform a measurement of the target gas based on the respective target gas sensitivity

FIG. 5

GAS CONCENTRATION SENSOR AND SENSOR CALIBRATION WITHOUT USE OF A TARGET GAS

BACKGROUND

There is an increasing demand for reducing the consumption of petroleum and shifting to using green energy. For example, hydrogen generated by wind turbines is considered as a possible green fuel for automotive applications.

Sensors may be required to detect any leaking hydrogen to avoid the formation of oxyhydrogen. Sensors for measuring a gas property, which may also be called gas sensors, may have a cross-sensitivity to different environment characteristics, such as humidity, temperature, and/or flow and concentration of the gas to be sensed. In some cases, dedicated sensors for these additional properties may have to be included in order to differentiate the signal of interest. For example, a complementary temperature sensor may have to be added. This may lead to a complex device, where different dies or sensing elements have to be combined inside a package.

SUMMARY

In some implementations, a sensor calibration system includes a first gas concentration sensor configured to measure a thermal conductivity of a target gas, wherein the first gas concentration sensor comprises: a housing comprising a reference chamber containing a reference gas and a measurement chamber containing a measurement gas, wherein the reference gas has a first thermal conductivity profile and the measurement gas has a second thermal conductivity profile that is different from the first thermal conductivity profile, wherein the first thermal conductivity profile and the second thermal conductivity profile are dependent on a first environmental stimulus and a second environmental stimulus, wherein the reference chamber is a closed chamber containing the reference gas and the measurement chamber is an open chamber exposed to the measurement gas; and a calibration circuit configured to acquire a first plurality of measurements, wherein the calibration circuit acquires the first plurality of measurements while the first environmental stimulus of the reference chamber and the measurement chamber is varied and while the second environmental stimulus of the reference chamber and the measurement chamber is fixed, wherein each measurement of the first plurality of measurements is representative of a difference in thermal conductivity between a thermal conductivity of the reference gas and a thermal conductivity of the measurement gas, wherein each measurement of the first plurality of measurements corresponds to a different value of the first environmental stimulus, and wherein the calibration circuit is configured to determine a first thermal conductivity sensitivity of the first gas concentration sensor based on the first plurality of measurements.

In some implementations, a sensor calibration system includes a gas concentration sensor configured to measure a thermal conductivity of a target gas, wherein the gas concentration sensor comprises: a housing comprising a reference chamber containing a reference gas and a measurement chamber containing a measurement gas, wherein the reference gas has a first thermal conductivity profile and the measurement gas has a second thermal conductivity profile that is different from the first thermal conductivity profile, wherein the first thermal conductivity profile and the second thermal conductivity profile are dependent on a first environmental stimulus and a second environmental stimulus, wherein the reference chamber is a closed chamber and the measurement chamber is an open chamber exposed to the measurement gas; and a calibration circuit configured to acquire a first plurality of measurements while the first environmental stimulus of the reference chamber and the measurement chamber is varied and while the second environmental stimulus of the reference chamber and the measurement chamber is fixed, wherein each measurement of the first plurality of measurements is representative of a difference in thermal conductivity between a thermal conductivity of the reference gas and a thermal conductivity of the measurement gas, wherein each measurement of the first plurality of measurements corresponds to a different value of the first environmental stimulus, and wherein the calibration circuit is configured to determine a target gas sensitivity of the gas concentration sensor to the target gas based on the first plurality of measurements.

In some implementations, a sensor calibration system includes a first gas concentration sensor configured to measure a thermal conductivity of a target gas, wherein the first gas concentration sensor comprises a first housing comprising a first measurement chamber; a second gas concentration sensor configured to measure the thermal conductivity of the target gas, wherein the second gas concentration sensor comprises a second housing comprising a second measurement chamber; and a calibration circuit configured to, while the first measurement chamber contains a measurement gas, acquire a first plurality of measurements from the first gas concentration sensor and, while the second measurement chamber contains the measurement gas, acquire a second plurality of measurements from the second gas concentration sensor, wherein the target gas and the measurement gas are different gases, wherein the calibration circuit acquires the first plurality of measurements while a pressure inside the first measurement chamber is varied and while a temperature inside the first measurement chamber is fixed, wherein the calibration circuit acquires the second plurality of measurements while a pressure inside the second measurement chamber is varied and while a temperature inside the second measurement chamber is fixed, wherein each measurement of the first plurality of measurements corresponds to a different value of the pressure, wherein each measurement of the second plurality of measurements corresponds to a different value of the pressure, wherein the calibration circuit is configured to determine a first thermal conductivity sensitivity of the first gas concentration sensor based on the first plurality of measurements, wherein the calibration circuit is configured to determine a second thermal conductivity sensitivity of the second gas concentration sensor based on the second plurality of measurements, wherein, while the first measurement chamber is exposed to the target gas and a concentration of the target gas in the first measurement chamber is varied, the calibration circuit is configured to acquire a third plurality of measurements, wherein each measurement of the third plurality of measurements corresponds to a different concentration of the target gas, wherein the calibration circuit is configured to determine a first target gas sensitivity of the first gas concentration sensor to the target gas based on the third plurality of measurements, wherein the calibration circuit is configured to calculate a correction factor based on the first thermal conductivity sensitivity and the first target gas sensitivity, wherein the calibration circuit is configured to calculate a second target gas sensitivity of the second gas concentration sensor based on the second thermal conductivity sensitivity and the correction factor, and wherein the calibration circuit is configured to calibrate the second gas concentration sensor for performing a measurement of the target gas based on the second target gas sensitivity.

In some implementations, a method of calibrating a plurality of gas concentration sensors to measure a concentration of a target gas includes determining a thermal conductivity sensitivity for each gas concentration sensor of the plurality of gas concentration sensors while not exposing the plurality of gas concentration sensors to the target gas; determining a target gas sensitivity for each gas concentration sensor of a first subset of the plurality of gas concentration sensors while exposing the first subset of the plurality of gas concentration sensors to the target gas; calculating a plurality of correction factors, including calculating a correction factor for each gas concentration sensor of the first subset of the plurality of gas concentration sensors, wherein the correction factor is calculated for each gas concentration sensor of the first subset of the plurality of gas concentration sensors based on a respective thermal conductivity sensitivity and a respective target gas sensitivity; calculating an average correction factor as an average of the plurality of correction factors; determining a target gas sensitivity for each gas concentration sensor of a remaining subset of the plurality of gas concentration sensors without exposing the remaining subset of the plurality of gas concentration sensors to the target gas, wherein determining the target gas sensitivity for each gas concentration sensor of the remaining subset of the plurality of gas concentration sensors includes: calculating a respective target gas sensitivity based on a respective thermal conductivity sensitivity of a corresponding gas concentration sensor of the remaining subset and based on the average correction factor; and calibrating each gas concentration sensor of the remaining subset of the plurality of gas concentration sensors with the respective target gas sensitivity in order for each gas concentration sensor of the remaining subset of the plurality of gas concentration sensors to perform a measurement of the target gas based on the respective target gas sensitivity.

BRIEF DESCRIPTION OF THE DRAWINGS

Implementations are described herein with reference to the appended drawings.

FIG. 5 is a flowchart of an example process associated with calibrating a plurality of gas concentration sensors.

DETAILED DESCRIPTION

Figure 1:
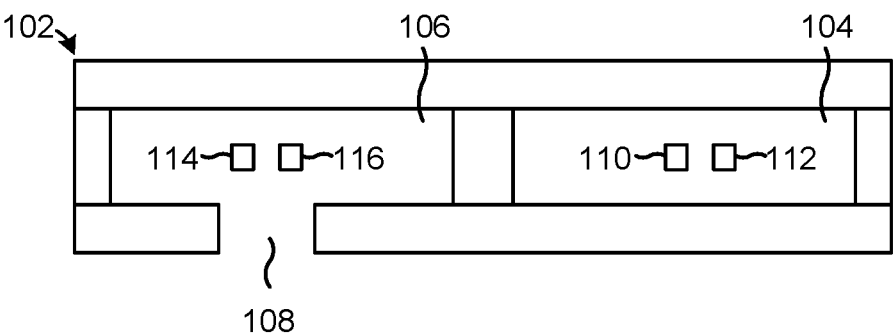
FIG. 1 illustrates a gas sensor according to one or more implementations.

In the following, details are set forth to provide a more thorough explanation of example implementations. However, it will be apparent to those skilled in the art that these implementations may be practiced without these specific details. In other instances, well-known structures and devices are shown in block diagram form or in a schematic view, rather than in detail, in order to avoid obscuring the implementations. In addition, features of the different implementations described hereinafter may be combined with each other, unless specifically noted otherwise.

Further, equivalent or like elements or elements with equivalent or like functionality are denoted in the following description with equivalent or like reference numerals. As the same or functionally equivalent elements are given the same reference numbers in the figures, a repeated description for elements provided with the same reference numbers may be omitted. Hence, descriptions provided for elements having the same or like reference numbers are mutually interchangeable.

The orientations of the various elements in the figures are shown as examples, and the illustrated examples may be rotated relative to the depicted orientations. The descriptions provided herein, and the claims that follow, pertain to any structures that have the described relationships between various features, regardless of whether the structures are in the particular orientation of the drawings, or are rotated relative to such orientation. Similarly, spatially relative terms, such as "top," "bottom," "below," "beneath," "lower," "above," "upper," "middle," "left," and "right," are used herein for ease of description to describe one element's relationship to one or more other elements as illustrated in the figures. The spatially relative terms are intended to encompass different orientations of the element, structure, and/or assembly in use or operation in addition to the orientations depicted in the figures. A structure and/or assembly may be otherwise oriented (rotated 90 degrees or at other orientations), and the spatially relative descriptors used herein may be interpreted accordingly. Furthermore, the cross-sectional views in the figures only show features within the planes of the cross-sections, and do not show materials behind the planes of the cross-sections, unless indicated otherwise, in order to simplify the drawings.

It will be understood that when an element is referred to as being "connected" or "coupled" to another element, it can be directly connected or coupled to the other element or intervening elements may be present. In contrast, when an element is referred to as being "directly connected" or "directly coupled" to another element, there are no intervening elements present. Other words used to describe the relationship between elements should be interpreted in a like fashion (e.g., "between" versus "directly between," "adjacent" versus "directly adjacent," etc.).

In implementations described herein or shown in the drawings, any direct electrical connection or coupling (e.g., any connection or coupling without additional intervening elements) may also be implemented by an indirect connection or coupling (e.g., a connection or coupling with one or more additional intervening elements, or vice versa) as long as the general purpose of the connection or coupling (e.g., to transmit a certain kind of signal or to transmit a certain kind of information) is essentially maintained. Features from different implementations may be combined to form further implementations. For example, variations or modifications described with respect to one of the implementations may also be applicable to other implementations unless noted to the contrary.

As used herein, the terms "substantially" and "approximately" mean "within reasonable tolerances of manufacturing and measurement." For example, the terms "substantially" and "approximately" may be used herein to account for small manufacturing tolerances or other factors (e.g., within 5%) that are deemed acceptable in the industry without departing from the aspects of the implementations described herein. For example, a resistor with an approximate resistance value may practically have a resistance within 5% of the approximate resistance value. As another example, a signal with an approximate signal value may practically have a signal value within 5% of the approximate signal value.

In the present disclosure, expressions including ordinal numbers, such as "first", "second", and/or the like, may modify various elements. However, such elements are not limited by such expressions. For example, such expressions do not limit the sequence and/or importance of the elements. Instead, such expressions are used merely for the purpose of distinguishing an element from the other elements. For example, a first box and a second box indicate different boxes, although both are boxes. For further example, a first element could be termed a second element, and similarly, a second element could also be termed a first element without departing from the scope of the present disclosure.

A "sensor" may refer to a component which converts a property to be measured to an electrical signal (e.g., a current signal or a voltage signal). The property to be measured may, for example, comprise a magnetic field, an electric field, an electromagnetic wave (e.g., a radio wave), a pressure, a force, a current, or a voltage, but is not limited thereto. A gas sensor may measure a property of a gas, such as a thermal conductivity of the gas. Based on the measured property, a presence of the gas can be detected. Additionally, based on the measured property, a concentration of the gas can be measured.

Gas sensors (e.g., microelectromechanical system (MEMS) thermal conductivity gas sensors) are typically produced in large batches and can be affected by production spread. For example, the gas sensors may have one or more characteristics that may vary slightly from production. Thus, each gas sensor may require sensitivity calibration to provide accurate measurements. Typical calibration methods include exposing each gas sensor to a target gas in a production environment. A calibration process conducted in this manner can be cumbersome, time consuming, and costly.

Some implementations disclosed herein are directed to performing a calibration process that does not require each gas sensor of a batch of gas sensors to be exposed to the target gas. Instead, only a subset of the gas sensors may be exposed to the target gas, and information obtained during exposure of the subset of the gas sensors to the target gas may be used to calibrate all the gas sensors in the batch of gas sensors.

For example, a MEMS thermal conductivity gas sensor may have a hermetic reference cavity filled with a defined reference gas at a defined pressure (e.g., nitrogen $N_2$ at 1 Bar). All temperature effects not related to gas thermal conductivity (e.g., a piezo-effect) may be removed from the sensor output. In other words, the MEMS thermal conductivity gas sensor may be isolated from all temperature effects not related to gas thermal conductivity. A thermal conductivity sensitivity of the MEMS thermal conductivity gas sensor may be determined by obtaining at least two measurements from the MEMS thermal conductivity gas sensor at different temperatures (e.g., at –20° C., 25° C., and 90° C.), at constant pressure and constant humidity. The thermal conductivity sensitivity may then be correlated to a sensitivity of the target gas to establish a constant correction factor that can be used to calibrate all the gas sensors in the batch of gas sensors. Thus, the calibration process can save time and manufacturing costs, while enabling each gas sensor to provide reliable and accurate measurements.

In some implementations, a gas sensor (e.g., a gas concentration sensor) may be configured to measure a thermal conductivity of a target gas. The gas sensor may include a housing that includes a measurement chamber that is open to an environment and is configured to contain a measurement gas, which may include the target gas. For example, the measurement gas may be an ambient gas, such as air. The gas sensor may include a resistive wire arranged in the measurement chamber. The gas sensor may measure the thermal conductivity of the measurement gas by heating up the resistive wire by applying a voltage across opposite ends of the resistive wire via a voltage source or injecting a current through the resistive wire via a current source. A resistance of the resistive wire may change based on the thermal conductivity of the measurement gas. For example, the resistive wire may release heat to the measurement gas based on the thermal conductivity of the measurement gas (e.g., the higher the thermal conductivity of a gas, the more heat is conducted by and released to the gas). In other words, a temperature change, and thus a resistance change, of the resistive wire may depend on a rate of thermal release of heat from the resistive wire to the measurement gas, which may depend on the thermal conductivity of the measurement gas. By measuring the resistance of the resistive wire, the thermal conductivity of the measurement gas may be measured and a concentration of the target gas in the measurement gas may be determined.

In some implementations, a gas sensor may measure the thermal conductivity of a target gas by heating up four resistive wires connected in a Wheatstone bridge configuration (e.g., a full-bridge resistive circuit), with two reference resistive wires isolated in a stable reference gas and two sense resistive wires exposed to the measurement gas, which may include the target gas. The four resistive wires may undergo a temperature change (e.g., a temperature increase) by applying a voltage across two input terminals of the Wheatstone bridge configuration. The two reference resistive wires may release heat to the stable reference gas based on a thermal conductivity of the stable reference gas (e.g., the higher the thermal conductivity of a gas, the more heat is conducted by and released to the gas). In other words, a temperature change, and thus a resistance change, of the two reference resistive wires may depend on a rate of thermal release of heat from the two reference resistive wires to the stable reference gas, which may depend on the thermal conductivity of the stable reference gas. The thermal conductivity of the stable reference gas is a known parameter. The two sense resistive wires may release heat to the measurement gas based on a thermal conductivity of the measurement gas. In other words, a temperature change, and thus a resistance change, of the two sense resistive wires may depend on a rate of thermal release of heat from the two sense resistive wires to the measurement gas, which may depend on the thermal conductivity of the measurement gas. The thermal conductivity of the measurement gas is an unknown parameter. For example, the thermal conductivity of the measurement gas may be related to a concentration of the target gas in the measurement gas.

The gas sensor may be configured to measure a differential signal output from the Wheatstone bridge configuration. The differential signal may be used as a measurement signal that represents a change in resistance of the sense resistive wires as compared to a change in resistance of the reference resistive wires generated by different rates of thermal release from the four resistive wires to the measurement gas and the stable reference gas, respectively. Thus, the concentration of the target gas may be measured based on the differential signal.

In some implementations, the gas sensor may include only a single half-bridge (e.g., one half-bridge resistive circuit). For example, only two resistive wires may be present, including a reference resistive wire arranged in the reference chamber and a sense resistive wire arranged in the measurement chamber. The single half-bridge may be configured to output a measurement signal from an output node arranged and coupled between the two resistive wires. The measurement signal may represent a change in resistance of the sense resistive wire as compared to a change in resistance of the reference resistive wire generated by different rates of thermal release from the two resistive wires to the measurement gas and the stable reference gas, respectively. Thus, the concentration of the target gas may be measured based on the measurement signal.

FIG. 1 illustrates a gas sensor 100 according to one or more implementations. The gas sensor 100 may be a thermal conductivity (TC) sensor that uses a known thermal conductivity of a reference gas to measure a concentration of a target gas contained within a measurement gas. For example, the gas sensor 100 may be configured to measure a thermal conductivity of the measurement gas based on a measurement signal, and determine the concentration of the target gas based on the thermal conductivity of the measurement gas.

The gas sensor 100 may include a housing 102 or casing that includes a reference chamber 104 configured to contain a reference gas, and a measurement chamber 106 configured to contain a measurement gas (e.g., an ambient gas) that is different from the reference gas. The reference gas may be oxygen or nitrogen, but not limited thereto. In some implementations, the reference gas may be a vacuum gas. The measurement gas may be the target gas or may include the target gas. The target gas may be absent from the reference gas. The reference chamber 104 may be a sealed chamber. For example, in some implementations, the reference chamber 104 may be hermetically sealed. In addition, the housing 102 may have an opening 108 (e.g., a conduit) that allows the measurement gas to enter the measurement chamber 106. Thus, the opening 108 may be provided for fluidly connecting the measurement chamber 106 to the measurement gas.

The gas sensor 100 may include a plurality of resistive elements, such as piezoresistive wires. The plurality of resistive elements may be substantially identical in resistivity when the gas sensor 100 is in an off state (e.g., when an input supply voltage is not applied to the plurality of resistive elements). In some implementations, the gas sensor 100 may include a first piezoresistive wire 110, a second piezoresistive wire 112, a third piezoresistive wire 114, and a fourth piezoresistive wire 116. The first piezoresistive wire 110 may be arranged in the reference chamber 104 and may be exposed to the reference gas, the second piezoresistive wire 112 may be arranged in the reference chamber 104 and may be exposed to the reference gas, the third piezoresistive wire 114 may be arranged in the measurement chamber 106 and may be exposed to the measurement gas, and the fourth piezoresistive wire 116 arranged in the measurement chamber 106 and may be exposed to the measurement gas.

The plurality of resistive elements may be provided in a resistive bridge circuit, such as a full-bridge circuit (e.g., a Wheatstone bridge). In other words, the plurality of resistive elements may be connected in a full-bridge configuration that includes two input terminals, to which an input voltage is applied, and two output terminals, from which a differential signal (e.g., a differential voltage) is output as a measurement signal. In other words, the full-bridge circuit may be configured to receive the input voltage and generate the differential signal at a differential output of the resistive bridge circuit based on the input voltage. The first piezoresistive wire 110 and the second piezoresistive wire 112 may be arranged on opposite segments of the full-bridge circuit. For example, the full-bridge circuit may include two half-bridges, including a first half-bridge and a second half-bridge. The first piezoresistive wire 110 may be arranged in the first half-bridge and the second piezoresistive wire 112 may be arranged in the second half-bridge. The first piezoresistive wire 110 may be arrange diagonally across from the second piezoresistive wire 112. The third piezoresistive wire 114 and the fourth piezoresistive wire 116 may also be arranged on opposite segments of the full-bridge circuit. For example, the third piezoresistive wire 114 may be arranged in the first half-bridge and the fourth piezoresistive wire 116 may be arranged in the second half-bridge. The third piezoresistive wire 114 may be arrange diagonally across from the fourth piezoresistive wire 116. Thus, each half-bridge is formed by one measurement piezoresistive wire and one reference piezoresistive wire.

In some implementations, only a single half-bridge may be used. For example, the plurality of resistive elements may include only two resistive wires. In this case, the resistive bridge circuit may only include the first piezoresistive wire 110 and the third piezoresistive wire 114, for example. The single half-bridge may be configured to output a measurement signal from an output node arranged and coupled between the two resistive wires. The measurement signal may represent a change in resistance of the first piezoresistive wire 110 as compared to a change in resistance of the third piezoresistive wire 114 generated by different rates of thermal release from the two resistive wires to the measurement gas and the reference gas, respectively. Thus, the concentration of the target gas may be measured based on the measurement signal.

As indicated above, FIG. 1 is provided as an example. Other examples may differ from what is described with regard to FIG. 1. The number and arrangement of devices and components shown in FIG. 1 are provided as an example. In practice, there may be additional devices or components, fewer devices or components, different devices or components, or differently arranged devices or components than those shown in FIG. 1.

Figure 2:
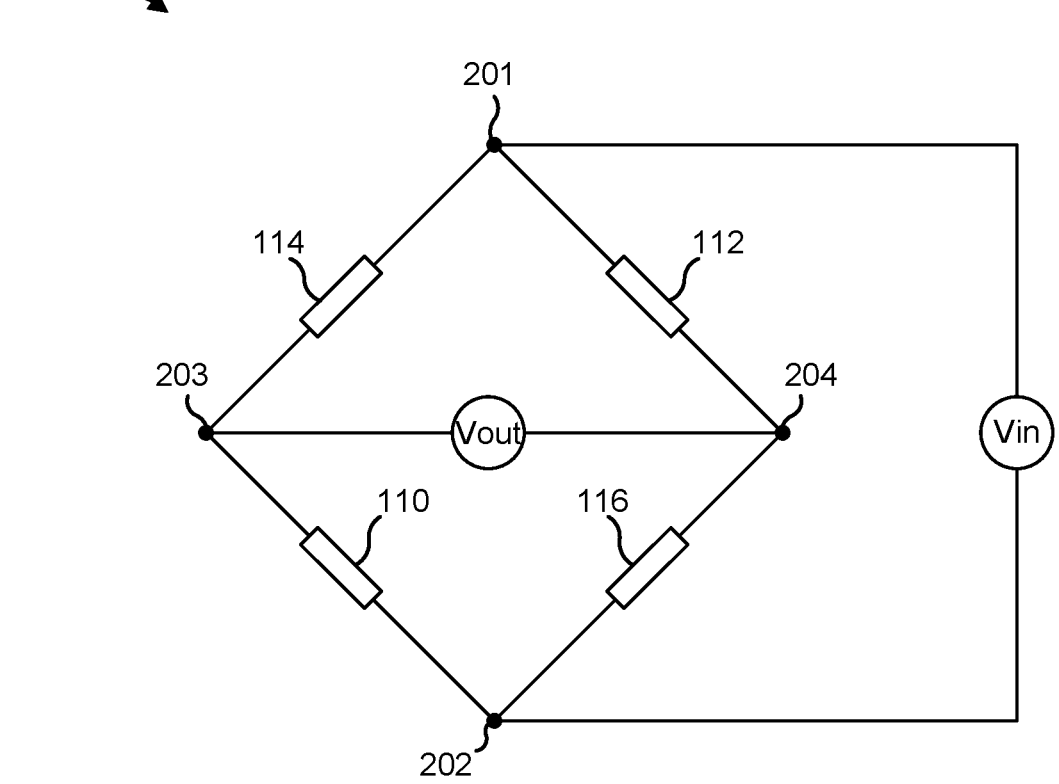
FIG. 2 illustrates a resistive bridge circuit according to one or more implementations.

FIG. 2 illustrates a resistive bridge circuit 200 according to one or more implementations. The resistive bridge circuit 200 may include the first piezoresistive wire 110, the second piezoresistive wire 112, the third piezoresistive wire 114, and the fourth piezoresistive wire 116 connected in a full-bridge configuration. The resistive bridge circuit 200 includes a first half-bridge on a left side and a second half-bridge on a right side. The first piezoresistive wire 110 may be arranged in the first half-bridge and the second piezoresistive wire 112 may be arranged in the second half-bridge. The first piezoresistive wire 110 may be arrange diagonally across from the second piezoresistive wire 112. The third piezoresistive wire 114 and the fourth piezoresistive wire 116 may also be arranged on opposite segments of the full-bridge circuit. For example, the third piezoresistive wire 114 may be arranged in the first half-bridge and the fourth piezoresistive wire 116 may be arranged in the second half-bridge. The third piezoresistive wire 114 may be arrange diagonally across from the fourth piezoresistive wire 116. Thus, each half-bridge is formed by one measurement piezoresistive wire and one reference piezoresistive wire.

The resistive bridge circuit 200 may include two input terminals, including a first input terminal 201 and a second input terminal 202. An input voltage Vin may be applied to the first input terminal 201 and the second input terminal 202. In other words, the input voltage Vin is applied across the two input terminals. A voltage level of the input voltage Vin may be controlled by a controller. The resistive bridge circuit 200 may further include two output terminals, including a first output terminal 203 and a second output terminal 204. Applying the input voltage Vin to the two input terminals cases the resistive bridge circuit 200 to generate a differential signal Vout (e.g., an output voltage) at the two output terminals. The differential signal Vout may be measured across the two output terminals and may be used by the gas sensor 100 as a measurement signal.

The differential signal Vout may depend on the voltage level of the input voltage Vin and respective resistances of the first piezoresistive wire 110, the second piezoresistive wire 112, the third piezoresistive wire 114, and the fourth piezoresistive wire 116. For example, the first piezoresistive wire 110, the second piezoresistive wire 112, the third piezoresistive wire 114, and the fourth piezoresistive wire 116 may undergo a temperature change (e.g., a temperature increase) by applying or by increasing the input voltage Vin across the two input terminals 201 and 202 of the resistive bridge circuit 200. Alternatively, the piezoresistive wires 110, 112, 114, and 116 may undergo a temperature decrease by either decreasing the input voltage Vin or removing the input voltage Vin.

When applying the input voltage Vin (e.g., from an off-state) or increasing the input voltage Vin, the piezoresistive wires 110, 112, 114, and 116 may heat up depending on the voltage level of the input voltage Vin. A temperature change of the piezoresistive wires 110, 112, 114, and 116 may occur at different rates based on an exposure of the first piezoresistive wire 110 and the second piezoresistive wire 112 to the reference gas and based on an exposure of the third piezoresistive wire 114 and the fourth piezoresistive wire 116 to the measurement gas.

For example, the first piezoresistive wire 110 and the second piezoresistive wire 112 may release heat to the reference gas based on a thermal conductivity of the reference gas. In other words, a temperature change, and thus a resistance change, of the first piezoresistive wire 110 and the second piezoresistive wire 112 may depend on a rate of thermal release of heat from the first piezoresistive wire 110 and the second piezoresistive wire 112 to the reference gas, which may depend on the thermal conductivity of the reference gas.

The third piezoresistive wire 114 and the fourth piezoresistive wire 116 may release heat to the measurement gas based on a thermal conductivity of the measurement gas. In other words, a temperature change, and thus a resistance change, of the third piezoresistive wire 114 and the fourth piezoresistive wire 116 may depend on a rate of thermal release of heat from the third piezoresistive wire 114 and the fourth piezoresistive wire 116 to the measurement gas, which may depend on the thermal conductivity of the measurement gas, which may be related to a concentration of the target gas in the measurement gas.

The gas sensor 100 may be configured to measure the differential signal Vout output from the resistive bridge circuit 200. The differential signal Vout may represent a change in resistance of the third piezoresistive wire 114 and the fourth piezoresistive wire 116 relative to a change in resistance of the first piezoresistive wire 110 and the second piezoresistive wire 112 produced by different rates of thermal release from the piezoresistive wires to the measurement gas and the reference gas, respectively. Thus, the concentration of the target gas may be measured based on the differential signal Vout.

As indicated above, FIG. 2 is provided as an example. Other examples may differ from what is described with regard to FIG. 2.

Figure 3:
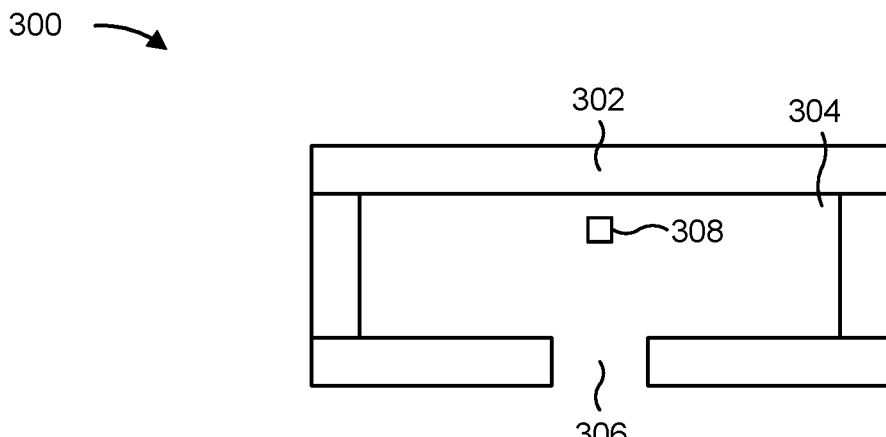
FIG. 3 illustrates a gas sensor according to one or more implementations.

FIG. 3 illustrates a gas sensor 300 according to one or more implementations. The gas sensor 300 may be a TC sensor that measures a thermal conductivity of the measurement gas based on a measurement signal, and determine the concentration of a target gas based on the thermal conductivity of the measurement gas.

The gas sensor may include a housing 302 or casing that includes a measurement chamber 304 configured to contain a measurement gas (e.g., an ambient gas). The measurement gas may be the target gas or may include the target gas. In addition, the housing 302 may have an opening 306 (e.g., a conduit) that allows the measurement gas to enter the measurement chamber 304. Thus, the opening 306 may be provided for fluidly connecting the measurement chamber 304 to the measurement gas.

The gas sensor 300 may include a resistive element, such as a piezoresistive wire 308, that is configured to be exposed to the measurement gas. The gas sensor 300 may measure the thermal conductivity of the measurement gas by heating up the piezoresistive wire 308 by applying a voltage across opposite ends of the piezoresistive wire 308 via a voltage source or injecting a current through the piezoresistive wire 308 via a current source. A resistance of the piezoresistive wire 308 may change based on the thermal conductivity of the measurement gas. For example, the piezoresistive wire 308 may release heat to the measurement gas based on the thermal conductivity of the measurement gas. In other words, a temperature change, and thus a resistance change, of the piezoresistive wire 308 may depend on a rate of thermal release of heat from the piezoresistive wire 308 to the measurement gas, which may depend on the thermal conductivity of the measurement gas. By measuring the resistance of the piezoresistive wire 308, the thermal conductivity of the measurement gas may be measured and a concentration of the target gas in the measurement gas may be determined.

As indicated above, FIG. 3 is provided as an example. Other examples may differ from what is described with regard to FIG. 3.

Figure 4:
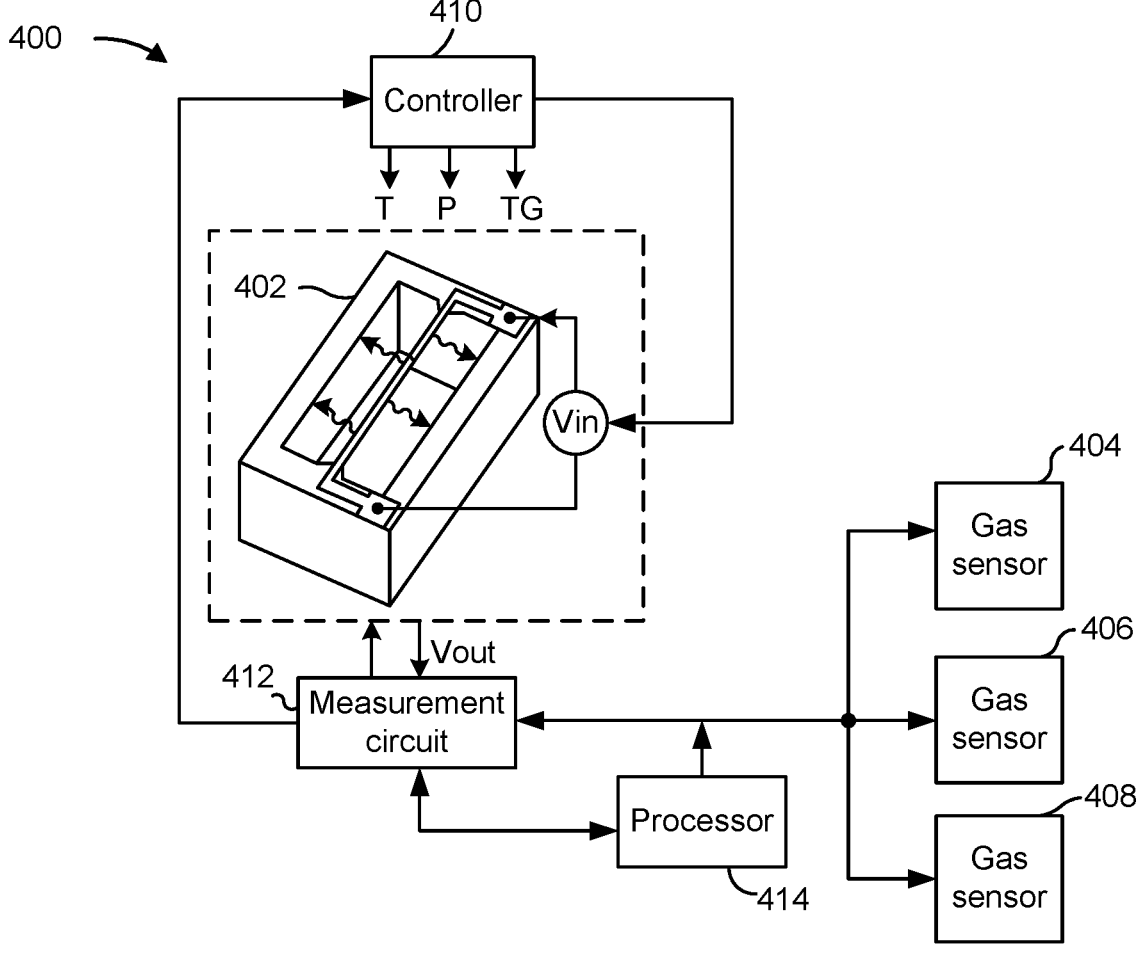
FIG. 4 is schematic block diagram of a sensor calibration system according to one or more implementations.

FIG. 4 is schematic block diagram of a sensor calibration system 400 according to one or more implementations. The sensor calibration system 400 may include a plurality of gas concentration sensors 402, 404, 406, and 408. The plurality of gas concentration sensors 402, 404, 406, and 408 may be part of a same production batch. Additionally, a first subset of the plurality of gas concentration sensors (e.g., gas concentration sensors 402 and 404) may be exposed to a target gas during a calibration process and a second subset of the plurality of gas concentration sensors (e.g., gas concentration sensors 406 and 408) may be calibrated without being exposed to the target gas during the calibration process. For example, information obtained from the first subset of the plurality of gas concentration sensors during exposure to the target gas may be used to calibrate all of the gas concentration sensors in the production batch, including those gas concentration sensors that were not exposed to the target gas. The plurality of gas concentration sensors 402, 404, 406, and 408 may be similar to the gas sensor 100 described in connection with FIGS. 1 and 2. Alternatively, the plurality of gas concentration sensors 402, 404, 406, and 408 may be similar to the gas sensor 300 described in connection with FIG. 3.

The sensor calibration system 400 may include calibration circuit that includes a controller 410, a measurement circuit

412, and a processor 414. The controller 410 may control the input voltage Vin supplied to a device under test (DUT), such as the gas concentration sensor 402. The controller 410 may also control a first environmental stimulus and a second environmental stimulus to which the DUT is exposed according to the calibration process. For example, the first environmental stimulus may be a temperature T and the second environmental stimulus may be a pressure P (e.g., an atmospheric pressure in Bar) and/or humidity.

The measurement circuit 412 may be configured to acquire a plurality of measurements from a measurement signal (e.g., output signal) that is generated by the DUT in response to the input voltage Vin being applied to the DUT (e.g., in response to the input voltage Vin being applied across two input terminals of the DUT). For example, the measurement circuit 412 may include an analog-to-digital converter (ADC) that is configured to sample the measurement signal to acquire the plurality of measurements (e.g., a plurality of measurement samples). The measurement circuit 412 may also include a memory device that is configured to store the plurality of measurements. The measurement circuit 412 may be configured to provide the plurality of measurements to the processor 414. The processor 414 may use the plurality of measurements from each DUT to calibrate each of the plurality of gas concentration sensors 402, 404, 406, and 408. For example, the processor 414 may calculate a constant correction factor (e.g., an average correction factor) to be used for calibrating each of the plurality of gas concentration sensors 402, 404, 406, and 408. The processor 414 may use the constant correction factor to determine a respective target gas sensitivity for each of the gas concentration sensors in the production batch. Measurement circuitry of each of the gas concentration sensors in the production batch may then be calibrated according to the respective target gas sensitivity. For example, the respective target gas sensitivity for a gas concentration sensor may be stored in the measurement circuitry (e.g., on chip) of the gas concentration sensor and used by the measurement circuitry for calibration during operation.

As noted above, in some implementations, the plurality of gas concentration sensors 402, 404, 406, and 408 may be similar to the gas sensor 100 described in connection with FIGS. 1 and 2. Accordingly, the plurality of gas concentration sensors 402, 404, 406, and 408 each have a reference chamber 104 containing a reference gas and a measurement chamber 106 containing a measurement gas. The reference chamber 104 is a closed chamber containing the reference gas and the measurement chamber 106 is an open chamber exposed to the measurement gas. The reference gas may have a first thermal conductivity profile (e.g., a characteristic curve) and the measurement gas may have a second thermal conductivity profile that is different from the first thermal conductivity profile. In addition, the first thermal conductivity profile and the second thermal conductivity profile are dependent on a first environmental stimulus and a second environmental stimulus.

The reference gas and the measurement gas may be different from the target gas (e.g., the target gas, the reference gas, and the measurement gas are different gases during the calibration process). For example, the target gas may be helium gas or hydrogen gas, the reference gas may be oxygen gas, nitrogen gas, or air, and the measurement gas may be oxygen gas, nitrogen gas, or air.

In some implementations, the first environmental stimulus is temperature and the second environmental stimulus is pressure. In some implementations, the first environmental stimulus is pressure and the second environmental stimulus is temperature. In some implementations, the first environmental stimulus is humidity and the second environmental stimulus is temperature. A thermal conductivity of the reference gas may depend on the first environmental stimulus, the second environmental stimulus, and the first thermal conductivity profile. A thermal conductivity of the measurement gas may depend on the first environmental stimulus, the second environmental stimulus, and the second thermal conductivity profile.

During a first subprocess of the calibration process, the calibration circuit may be configured to, while the first environmental stimulus of the reference chamber and the measurement chamber is varied and while the second environmental stimulus of the reference chamber and the measurement chamber is fixed, acquire a first plurality of measurements from the DUT (e.g., the gas concentration sensor 402). For example, for a first measurement, the controller 410 may set the first environmental stimulus to a first value (e.g., a first temperature value) and may set the second environmental stimulus to a fixed value (e.g., a fixed pressure value). The measurement circuit 412 may obtain a first measurement from the measurement signal Vout of the DUT. For a second measurement, the controller 410 may set the first environmental stimulus to a second value (e.g., a second temperature value) and may set the second environmental stimulus to the fixed value (e.g., the fixed pressure value). The measurement circuit 412 may obtain a second measurement from the measurement signal Vout of the DUT. The calibration circuit may obtain additional measurements from the DUT by adjusting the first environmental stimulus and sampling the measurement signal Vout for each value of the first environmental stimulus. As a result, measurement circuit 412 obtains the first plurality of measurements from the DUT over a range of values of the first environmental stimulus. For example, each measurement of the first plurality of measurements may correspond to a different value of the first environmental stimulus. Each measurement of the first plurality of measurements may be representative of a difference in thermal conductivity between the thermal conductivity of the reference gas and the thermal conductivity of the measurement gas.

The processor 414 may be configured to determine a thermal conductivity sensitivity of the DUT (e.g., the gas concentration sensor 402) based on the first plurality of measurements acquired from the DUT. The thermal conductivity sensitivity may be a measure of mV/(mW/m/K), where mV denote millivolts, mW denotes milliwatts, m denotes meters, and K denotes Kelvin. The processor 414 may determine the thermal conductivity sensitivity of the DUT based on calculating an estimated slope of the first plurality of measurements. In some implementations, the thermal conductivity sensitivity of the DUT is equal to the estimated slope of the first plurality of measurements.

A process for determining the thermal conductivity sensitivity may be performed for each gas concentration sensor in the production batch. For example, the first plurality of measurements may be individually obtained for the plurality of gas concentration sensors 402, 404, 406, and 408, and the thermal conductivity sensitivity may be determined for each of the plurality of gas concentration sensors 402, 404, 406, and 408. Thus, the thermal conductivity sensitivity may be determined for each of the plurality of gas concentration sensors 402, 404, 406, and 408 without introducing the target gas into the measurement chamber, with the exception of trace amounts of the target gas that may be present in a gas mixture of the measurement gas, such as air.

During a second subprocess of the calibration process, a subset of gas concentration sensors (e.g., a first subset of gas concentration sensors, such as gas concentration sensors 402 and 404) may be used. During the second subprocess, the measurement chambers of the first subset of gas concentration sensors are exposed to the target gas for determining a target gas sensitivity measured in mV/% TG, where TG denotes "target gas." For example, the calibration circuit may be configured to, while a measurement chamber of a DUT of the first subset (e.g., the gas concentration sensor 402) is exposed to the target gas and a concentration of the target gas in the measurement chamber is varied, acquire a second plurality of measurements. During the second subprocess, the first environmental stimulus and the second environmental stimulus are held constant. In other words, the first environmental stimulus of the reference chamber and the measurement chamber is fixed and the second environmental stimulus of the reference chamber and the measurement chamber is fixed while the calibration circuit acquires the second plurality of measurements.

For example, for a first measurement, the controller 410 may set the concentration of the target gas to a first value (e.g., a first concentration value). The measurement circuit 412 may obtain a first measurement from the measurement signal Vout of the DUT. For a second measurement, the controller 410 may set the concentration of the target gas to a second value (e.g., a second concentration value) that is different from the first value. The measurement circuit 412 may obtain a second measurement from the measurement signal Vout of the DUT. The calibration circuit may obtain additional measurements from the DUT by adjusting the concentration of the target gas and sampling the measurement signal Vout for each value of the concentration of the target gas. As a result, measurement circuit 412 obtains the second plurality of measurements from the DUT over a range of values of the concentration of the target gas. For example, each measurement of the second plurality of measurements may correspond to a different concentration value of the target gas for a particular gas concentration sensor of the first subset of gas concentration sensors.

The processor 414 may be configured to determine a target gas sensitivity of the DUT (e.g., the gas concentration sensor 402) to the target gas based on the second plurality of measurements based on the second plurality of measurements acquired from the DUT. The processor 414 may determine the target gas sensitivity of the DUT based on calculating an estimated slope of the second plurality of measurements. In some implementations, the target gas sensitivity of the DUT is equal to the estimated slope of the second plurality of measurements.

A process for determining the target gas sensitivity may be performed for each gas concentration sensor in the first subset of gas concentration sensors. For example, the second plurality of measurements may be individually obtained for the gas concentration sensors 402 and 404, and the target gas sensitivity may be determined for each of the gas concentration sensors 402 and 404 based on a respective second plurality of measurements. On the other hand, the second plurality of measurements may be obtained for the second subset of gas concentration sensors, such as gas concentration sensors 406 and 408. Thus, only the first subset of gas concentration sensors are exposed to the target gas that is varied in concentration.

The calibration circuit may be configured to calibrate the plurality of gas concentration sensors 402, 404, 406, and 408 for performing a respective measurement of the target gas based on the target gas sensitivities for the first subset of gas concentration sensors. For example, the target gas sensitivity determined for the gas concentration sensor 402 and the target gas sensitivity determined for the gas concentration sensor 402 may be used to calibrate the plurality of gas concentration sensors 402, 404, 406, and 408 for performing a respective measurement of the target gas. For example, the processor 414 may calculate a correction factor corresponding to the gas concentration sensor 402 based on the thermal conductivity sensitivity and the target gas sensitivity of the gas concentration sensor 402, by dividing the thermal conductivity sensitivity by the target gas sensitivity. In other words, the correction factor may be equal to a quotient of the thermal conductivity sensitivity divided by the target gas sensitivity. The processor 414 may calculate a correction factor for each gas concentration sensor of the first subset of gas concentration sensors by dividing a respective thermal conductivity sensitivity determined in the first subprocess by a respective target gas sensitivity determined in the second subprocess. The processor 414 may calculate an average correction factor as an average of the correction factors corresponding to the first subset of gas concentration sensors.

The processor 414 may calculate a respective target gas sensitivity for each of the gas concentration sensors of the second subset of gas concentration sensors based on the average correction factor. For example, the processor 414 may calculate a target gas sensitivity for the gas concentration sensor 406 by dividing the thermal conductivity sensitivity of the gas concentration sensor 406 determined in the first subprocess by the average correction factor. In other words, the target gas sensitivity of the gas concentration sensor 406 may be equal to a quotient of the thermal conductivity sensitivity of the gas concentration sensor 406 determined in the first subprocess divided by the average correction factor determined in the second subprocess. The processor 414 may calibrate the gas concentration sensor 406 for performing a measurement of the target gas based on the target gas sensitivity calculated for the gas concentration sensor 406. Thus, the first plurality of measurements obtained from the gas concentration sensor 406 during the first subprocess are used to determine the target gas sensitivity of the gas concentration sensor 406 in combination with the average correction factor determined in the second subprocess.

Similarly, the processor 414 may calculate a target gas sensitivity for the gas concentration sensor 408 by dividing the thermal conductivity sensitivity of the gas concentration sensor 408 determined in the first subprocess by the average correction factor. In other words, the target gas sensitivity of the gas concentration sensor 408 may be equal to a quotient of the thermal conductivity sensitivity of the gas concentration sensor 408 determined in the first subprocess divided by the average correction factor determined in the second subprocess. The processor 414 may calibrate the gas concentration sensor 408 for performing a measurement of the target gas based on the target gas sensitivity calculated for the gas concentration sensor 408. Thus, the first plurality of measurements obtained from the gas concentration sensor 408 during the first subprocess are used to determine the target gas sensitivity of the gas concentration sensor 408 in combination with the average correction factor determined in the second subprocess.

The target gas sensitivity determined during the second subprocess for each gas sensor of the first subset of gas concentration sensors may be used as a calibration input for a respective gas sensor of the first subset of gas concentration sensor. Thus, the processor 414 may calibrate the gas concentration sensor 402 for performing a measurement of the target gas based on the target gas sensitivity calculated for the gas concentration sensor 402 determined in the second subprocess. Similarly, the processor 414 may calibrate the gas concentration sensor 404 for performing a measurement of the target gas based on the target gas sensitivity calculated for the gas concentration sensor 404 determined in the second subprocess.

Each gas concentration sensor of the plurality of gas concentration sensors 402, 404, 406, and 408 are configured to compensate for a measurement of the target gas based on a respective target gas sensitivity programmed by the calibration circuit to generate a compensated measurement of the target gas. For example, during operation, the measurement signal Vout may be compensated by the measurement circuitry of the gas concentration sensor based on the target gas sensitivity.

As noted above, in some implementations, the plurality of gas concentration sensors 402, 404, 406, and 408 may be similar to the gas sensor 300 described in connection with FIG. 3. The first subprocess and the second subprocess may be performed in a similar manner described above for a production batch of gas sensors 300. When calibrating the production batch of gas sensors 300, the first environmental stimulus may be pressure and the second environmental stimulus may be temperature. For example, the gas concentration sensor 402, implemented with only one chamber as described in connection with the gas sensor 300, may be configured to measure a thermal conductivity of a target gas. Similarly, the gas concentration sensor 406, implemented with only one chamber as described in connection with the gas sensor 300, may be configured to measure the thermal conductivity of the target gas. The gas concentration sensor 402 may be among the first subset of gas concentration sensors and the gas concentration sensor 406 may be among the second subset of gas concentration sensors.

The calibration circuit may, while a first measurement chamber (e.g., measurement chamber 304) of the gas concentration sensor 402 contains a measurement gas, acquire a first plurality of measurements from the gas concentration sensor 402 and, while a second measurement chamber (e.g., measurement chamber 304) of the gas concentration sensor 406 contains the measurement gas, acquire a second plurality of measurements from the second gas concentration sensor. The target gas and the measurement gas are different gases.

The calibration circuit may acquire the first plurality of measurements while a pressure inside the first measurement chamber of the gas concentration sensor 402 is varied and while a temperature inside the first measurement chamber is fixed. For example, each measurement of the first plurality of measurements may correspond to a different value of the pressure.

Additionally, the calibration circuit may acquire the second plurality of measurements while a pressure inside the second measurement chamber of the gas concentration sensor 406 is varied and while a temperature inside the second measurement chamber is fixed. For example, each measurement of the second plurality of measurements may correspond to a different value of the pressure.

The calibration circuit may determine a first thermal conductivity sensitivity of the gas concentration sensor 402 based on the first plurality of measurements, and may determine a second thermal conductivity sensitivity of the gas concentration sensor 406 based on the second plurality of measurements. When the first environmental stimulus is pressure, a thermal conductivity sensitivity may be measured in $\mu V/mBar$, wherein u V denotes microvolts and mBar denotes millibar. The first thermal conductivity sensitivity may be determined from an estimated slope of the first plurality of measurements and the second thermal conductivity sensitivity may be determined from an estimated slope of the second plurality of measurements.

The calibration circuit may also determine the thermal conductivity sensitivity for the gas concentration sensors 404 and 408 in a similar manner by varying a pressure at a fixed temperature during exposure to the measurement gas.

The calibration circuit may, while the first measurement chamber of the gas concentration sensor 402 is exposed to the target gas and a concentration of the target gas in the first measurement chamber is varied at a fixed pressure and a fixed temperature, acquire a third plurality of measurements. For example, each measurement of the third plurality of measurements may correspond to a different concentration of the target gas. The calibration circuit may determine a first target gas sensitivity (e.g., mV/% TG) of the gas concentration sensor 402 to the target gas based on the third plurality of measurements. For example, the first target gas sensitivity may be determined from an estimated slope of the third plurality of measurements. The calibration circuit may determine a target gas sensitivity in a similar manner for each gas concentration sensor of the first subset of gas concentration sensors by exposing each gas concentration sensor of the first subset of gas concentration sensors to a variable concentration of the target gas at a fixed pressure and a fixed temperature. In contrast, the second subset of gas concentration sensors do no undergo this subprocess of target gas exposure.

The calibration circuit may calculate a correction factor based on the first thermal conductivity sensitivity and the first target gas sensitivity of the gas concentration sensor 402. Moreover, the calibration circuit may calculate a correction factor for each gas concentration sensor of the first subset of gas concentration sensors in a manner similarly described above, and calculate an average correction factor as an average of the correction factors of the first subset of gas concentration sensors.

The calibration circuit may calculate a second target gas sensitivity of the gas concentration sensor 406 based on the second thermal conductivity sensitivity and the correction factor of the gas concentration sensor 402. In particular, the calibration circuit may calculate the second target gas sensitivity of the gas concentration sensor 406 based on the second thermal conductivity sensitivity and the average correction factor in a manner similarly described above. Moreover, the calibration circuit may calculate a target gas sensitivity for each gas concentration sensor of the second subset of gas concentration sensors in a manner similarly described above by using the average correction factor.

The calibration circuit may calibrate the gas concentration sensor 406 for performing a measurement of the target gas based on the second target gas sensitivity. In particular, the calibration circuit may calibrate each gas concentration sensor of the second subset of gas concentration sensors for performing a respective measurement of the target gas based on each respective target gas sensitivity.

As indicated above, FIG. 4 is provided as an example. Other examples may differ from what is described with regard to FIG. 4. The number and arrangement of devices and components shown in FIG. 4 are provided as an example. In practice, there may be additional devices or components, fewer devices or components, different devices or components, or differently arranged devices or components than those shown in FIG. 4.

FIG. 5 is a flowchart of an example process 500 associated with calibrating a plurality of gas concentration sensors. In some implementations, one or more process blocks of FIG. 5 are performed by a sensor calibration system (e.g., sensor calibration system 400). Additionally, or alternatively, one or more process blocks of FIG. 5 may be performed by one or more components of the sensor calibration system 400, such as the controller 410, the measurement circuit 412, and/or the processor 414.

As shown in FIG. 5, process 500 may include determining a thermal conductivity sensitivity for each gas concentration sensor of the plurality of gas concentration sensors while not exposing the plurality of gas concentration sensors to the target gas (block 510).

As further shown in FIG. 5, process 500 may include determining a target gas sensitivity for each gas concentration sensor of a first subset of the plurality of gas concentration sensors while exposing the first subset of the plurality of gas concentration sensors to the target gas (block 520).

As further shown in FIG. 5, process 500 may include calculating a plurality of correction factors, including calculating a correction factor for each gas concentration sensor of the first subset of the plurality of gas concentration sensors. The correction factor may be calculated for each gas concentration sensor of the first subset of the plurality of gas concentration sensors based on a respective thermal conductivity sensitivity and a respective target gas sensitivity (block 530).

As further shown in FIG. 5, process 500 may include calculating an average correction factor as an average of the plurality of correction factors (block 540).

As further shown in FIG. 5, process 500 may include determining a target gas sensitivity for each gas concentration sensor of a remaining subset of the plurality of gas concentration sensors without exposing the remaining subset of the plurality of gas concentration sensors to the target gas. For example, the remaining subset of the plurality of gas concentration sensors may correspond to a second subset of gas concentration sensors. Determining the target gas sensitivity for each gas concentration sensor of the remaining subset of the plurality of gas concentration sensors may include calculating a respective target gas sensitivity based on a respective thermal conductivity sensitivity of a corresponding gas concentration sensor of the remaining subset and based on the average correction factor (block 550).

As further shown in FIG. 5, process 500 may include calibrating each gas concentration sensor of the remaining subset of the plurality of gas concentration sensors with the respective target gas sensitivity in order for each gas concentration sensor of the remaining subset of the plurality of gas concentration sensors to perform a measurement of the target gas based on the respective target gas sensitivity (block 560).

Process 500 may include additional implementations, such as any single implementation or any combination of implementations described below and/or in connection with one or more other processes described elsewhere herein.

In a first implementation, determining the thermal conductivity sensitivity for each gas concentration sensor of the plurality of gas concentration sensors may include acquiring a respective first plurality of measurements from each gas concentration sensor of the plurality of gas concentration sensors while exposing each gas concentration sensor of the plurality of gas concentration sensors to a measurement gas that is different from the target gas, while a first environmental stimulus is varied, and while a second environmental stimulus is fixed, and determining the thermal conductivity sensitivity for each gas concentration sensor of the plurality of gas concentration sensors based on an estimated slope of the respective first plurality of measurements.

In a second implementation, determining the target gas sensitivity for each gas concentration sensor of the first subset of the plurality of gas concentration sensors may include acquiring a respective second plurality of measurements from each gas concentration sensor of the first subset of the plurality of gas concentration sensors while a concentration of the target gas is varied, and determining the target gas sensitivity for each gas concentration sensor of the first subset of the plurality of gas concentration sensors based on an estimated slope of the respective second plurality of measurements.

Although FIG. 5 shows example blocks of process 500, in some implementations, process 500 includes additional blocks, fewer blocks, different blocks, or differently arranged blocks than those depicted in FIG. 5. Additionally, or alternatively, two or more of the blocks of process 500 may be performed in parallel.

The following provides an overview of some Aspects of the present disclosure:

Aspect 1: A sensor calibration system, comprising: a first gas concentration sensor configured to measure a thermal conductivity of a target gas, wherein the first gas concentration sensor comprises: a housing comprising a reference chamber containing a reference gas and a measurement chamber containing a measurement gas, wherein the reference gas has a first thermal conductivity profile and the measurement gas has a second thermal conductivity profile that is different from the first thermal conductivity profile, wherein the first thermal conductivity profile and the second thermal conductivity profile are dependent on a first environmental stimulus and a second environmental stimulus, wherein the reference chamber is a closed chamber containing the reference gas and the measurement chamber is an open chamber exposed to the measurement gas; and a calibration circuit configured to acquire a first plurality of measurements, wherein the calibration circuit acquires the first plurality of measurements while the first environmental stimulus of the reference chamber and the measurement chamber is varied and while the second environmental stimulus of the reference chamber and the measurement chamber is fixed, wherein each measurement of the first plurality of measurements is representative of a difference in thermal conductivity between a thermal conductivity of the reference gas and a thermal conductivity of the measurement gas, wherein each measurement of the first plurality of measurements corresponds to a different value of the first environmental stimulus, and wherein the calibration circuit is configured to determine a first thermal conductivity sensitivity of the first gas concentration sensor based on the first plurality of measurements.

Aspect 2: The sensor calibration system of Aspect 1, wherein the first environmental stimulus is temperature and the second environmental stimulus is pressure, wherein the first environmental stimulus is pressure and the second environmental stimulus is temperature, or wherein the first environmental stimulus is humidity and the second environmental stimulus is temperature.

Aspect 3: The sensor calibration system of any of Aspects 1-2, wherein the target gas, the reference gas, and the measurement gas are different gases.

Aspect 4: The sensor calibration system of Aspect 3, wherein the target gas is helium gas or hydrogen gas, the reference gas is oxygen gas, nitrogen gas, or air, and the measurement gas is oxygen gas, nitrogen gas, or air.

Aspect 5: The sensor calibration system of any of Aspects 1-4, wherein the thermal conductivity of the reference gas depends on the first environmental stimulus, the second environmental stimulus, and the first thermal conductivity profile, and the thermal conductivity of the measurement gas depends on the first environmental stimulus, the second environmental stimulus, and the second thermal conductivity profile.

Aspect 6: The sensor calibration system of any of Aspects 1-5, wherein the calibration circuit is configured to determine the first thermal conductivity sensitivity of the first gas concentration sensor based on an estimated slope of the first plurality of measurements.

Aspect 7: The sensor calibration system of Aspect 6, wherein the first thermal conductivity sensitivity is equal to the estimated slope of the first plurality of measurements.

Aspect 8: The sensor calibration system of any of Aspects 1-7, wherein, while the measurement chamber is exposed to the target gas and a concentration of the target gas in the measurement chamber is varied, the calibration circuit is configured to acquire a second plurality of measurements, wherein each measurement of the second plurality of measurements corresponds to a different concentration of the target gas, and wherein the calibration circuit is configured to determine a first target gas sensitivity of the first gas concentration sensor to the target gas based on the second plurality of measurements.

Aspect 9: The sensor calibration system of Aspect 8, wherein the first environmental stimulus of the reference chamber and the measurement chamber is fixed and the second environmental stimulus of the reference chamber and the measurement chamber is fixed while the calibration circuit acquires the second plurality of measurements.

Aspect 10: The sensor calibration system of Aspect 8, wherein the calibration circuit is configured to determine the first target gas sensitivity based on an estimated slope of the second plurality of measurements.

Aspect 11: The sensor calibration system of Aspect 8, wherein the calibration circuit is configured to calibrate the first gas concentration sensor for performing a measurement of the target gas based on the first target gas sensitivity.

Aspect 12: The sensor calibration system of Aspect 8, wherein the first gas concentration sensor is configured to compensate for a measurement of the target gas based on the first target gas sensitivity to generate a compensated measurement of the target gas.

Aspect 13: The sensor calibration system of Aspect 8, wherein the calibration circuit is configured to calculate a correction factor based on the first thermal conductivity sensitivity and the first target gas sensitivity, wherein the calibration circuit is configured to determine a second thermal conductivity sensitivity of a second gas concentration sensor, wherein the calibration circuit is configured to calculate a second target gas sensitivity of the second gas concentration sensor based on the second thermal conductivity sensitivity and the correction factor, and wherein the calibration circuit is configured to calibrate the second gas concentration sensor for performing a measurement of the target gas based on the second target gas sensitivity.

Aspect 14: The sensor calibration system of any of Aspects 1-13, wherein the first gas concentration sensor comprises: a first reference piezoresistive wire arranged in the reference chamber and exposed to the reference gas, wherein the first reference piezoresistive wire has a first resistance value based on the thermal conductivity of the reference gas; and a first measurement piezoresistive wire arranged in the measurement chamber, and exposed to the measurement gas, and connected to the first reference piezoresistive wire in a first half-bridge, wherein the first measurement piezoresistive wire has a second resistance value based on the thermal conductivity of the measurement gas, wherein, while a voltage is applied across the first half-bridge, the calibration circuit is configured to acquire the first plurality of measurements by sampling an output of the first half-bridge.

Aspect 15: The sensor calibration system of Aspect 14, wherein the first gas concentration sensor comprises: a second reference piezoresistive wire arranged in the reference chamber and exposed to the reference gas, wherein the second reference piezoresistive wire has a third resistance value based on the thermal conductivity of the reference gas; and a second measurement piezoresistive wire arranged in the measurement chamber, and exposed to the measurement gas, and connected to the second reference piezoresistive wire in a second half-bridge, wherein the second measurement piezoresistive wire has a fourth resistance value based on the thermal conductivity of the measurement gas, wherein the first half-bridge and the second half-bridge form a full bridge, and wherein, while the voltage is applied across the full bridge, the calibration circuit is configured to acquire the first plurality of measurements by sampling a differential output of the full bridge.

Aspect 16: A sensor calibration system, comprising: a gas concentration sensor configured to measure a thermal conductivity of a target gas, wherein the gas concentration sensor comprises: a housing comprising a reference chamber containing a reference gas and a measurement chamber containing a measurement gas, wherein the reference gas has a first thermal conductivity profile and the measurement gas has a second thermal conductivity profile that is different from the first thermal conductivity profile, wherein the first thermal conductivity profile and the second thermal conductivity profile are dependent on a first environmental stimulus and a second environmental stimulus, wherein the reference chamber is a closed chamber and the measurement chamber is an open chamber exposed to the measurement gas; and a calibration circuit configured to acquire a first plurality of measurements while the first environmental stimulus of the reference chamber and the measurement chamber is varied and while the second environmental stimulus of the reference chamber and the measurement chamber is fixed, wherein each measurement of the first plurality of measurements is representative of a difference in thermal conductivity between a thermal conductivity of the reference gas and a thermal conductivity of the measurement gas, wherein each measurement of the first plurality of measurements corresponds to a different value of the first environmental stimulus, and wherein the calibration circuit is configured to determine a target gas sensitivity of the gas concentration sensor to the target gas based on the first plurality of measurements.

Aspect 17: The sensor calibration system of Aspect 16, wherein the gas concentration sensor is configured to compensate for a measurement of the target gas based on the target gas sensitivity to generate a compensated measurement of the target gas.

Aspect 18: A sensor calibration system, comprising: a first gas concentration sensor configured to measure a thermal conductivity of a target gas, wherein the first gas concentration sensor comprises a first housing comprising a first measurement chamber; a second gas concentration sensor configured to measure the thermal conductivity of the target gas, wherein the second gas concentration sensor comprises a second housing comprising a second measurement chamber; and a calibration circuit configured to, while the first measurement chamber contains a measurement gas, acquire a first plurality of measurements from the first gas concentration sensor and, while the second measurement chamber contains the measurement gas, acquire a second plurality of measurements from the second gas concentration sensor, wherein the target gas and the measurement gas are different gases, wherein the calibration circuit acquires the first plurality of measurements while a pressure inside the first measurement chamber is varied and while a temperature inside the first measurement chamber is fixed, wherein the calibration circuit acquires the second plurality of measurements while a pressure inside the second measurement chamber is varied and while a temperature inside the second measurement chamber is fixed, wherein each measurement of the first plurality of measurements corresponds to a different value of the pressure, wherein each measurement of the second plurality of measurements corresponds to a different value of the pressure, wherein the calibration circuit is configured to determine a first thermal conductivity sensitivity of the first gas concentration sensor based on the first plurality of measurements, wherein the calibration circuit is configured to determine a second thermal conductivity sensitivity of the second gas concentration sensor based on the second plurality of measurements, wherein, while the first measurement chamber is exposed to the target gas and a concentration of the target gas in the first measurement chamber is varied, the calibration circuit is configured to acquire a third plurality of measurements, wherein each measurement of the third plurality of measurements corresponds to a different concentration of the target gas, wherein the calibration circuit is configured to determine a first target gas sensitivity of the first gas concentration sensor to the target gas based on the third plurality of measurements, wherein the calibration circuit is configured to calculate a correction factor based on the first thermal conductivity sensitivity and the first target gas sensitivity, wherein the calibration circuit is configured to calculate a second target gas sensitivity of the second gas concentration sensor based on the second thermal conductivity sensitivity and the correction factor, and wherein the calibration circuit is configured to calibrate the second gas concentration sensor for performing a measurement of the target gas based on the second target gas sensitivity.

Aspect 19: A method of calibrating a plurality of gas concentration sensors to measure a concentration of a target gas, the method comprising: determining a thermal conductivity sensitivity for each gas concentration sensor of the plurality of gas concentration sensors while not exposing the plurality of gas concentration sensors to the target gas; determining a target gas sensitivity for each gas concentration sensor of a first subset of the plurality of gas concentration sensors while exposing the first subset of the plurality of gas concentration sensors to the target gas; calculating a plurality of correction factors, including calculating a correction factor for each gas concentration sensor of the first subset of the plurality of gas concentration sensors, wherein the correction factor is calculated for each gas concentration sensor of the first subset of the plurality of gas concentration sensors based on a respective thermal conductivity sensitivity and a respective target gas sensitivity; calculating an average correction factor as an average of the plurality of correction factors; determining a target gas sensitivity for each gas concentration sensor of a remaining subset of the plurality of gas concentration sensors without exposing the remaining subset of the plurality of gas concentration sensors to the target gas, wherein determining the target gas sensitivity for each gas concentration sensor of the remaining subset of the plurality of gas concentration sensors includes: calculating a respective target gas sensitivity based on a respective thermal conductivity sensitivity of a corresponding gas concentration sensor of the remaining subset and based on the average correction factor; and calibrating each gas concentration sensor of the remaining subset of the plurality of gas concentration sensors with the respective target gas sensitivity in order for each gas concentration sensor of the remaining subset of the plurality of gas concentration sensors to perform a measurement of the target gas based on the respective target gas sensitivity.

Aspect 20: The method of Aspect 19, wherein determining the thermal conductivity sensitivity for each gas concentration sensor of the plurality of gas concentration sensors includes: acquiring a respective first plurality of measurements from each gas concentration sensor of the plurality of gas concentration sensors while exposing each gas concentration sensor of the plurality of gas concentration sensors to a measurement gas that is different from the target gas, while a first environmental stimulus is varied, and while a second environmental stimulus is fixed; and determining the thermal conductivity sensitivity for each gas concentration sensor of the plurality of gas concentration sensors based on an estimated slope of the respective first plurality of measurements.

Aspect 21: The method of any of Aspects 19-20, wherein determining the target gas sensitivity for each gas concentration sensor of the first subset of the plurality of gas concentration sensors includes: acquiring a respective second plurality of measurements from each gas concentration sensor of the first subset of the plurality of gas concentration sensors while a concentration of the target gas is varied; and determining the target gas sensitivity for each gas concentration sensor of the first subset of the plurality of gas concentration sensors based on an estimated slope of the respective second plurality of measurements.

Aspect 22: A system configured to perform one or more operations recited in one or more of Aspects 1-21.

Aspect 23: An apparatus comprising means for performing one or more operations recited in one or more of Aspects 1-21.

Aspect 24: A non-transitory computer-readable medium storing a set of instructions, the set of instructions comprising one or more instructions that, when executed by a device, cause the device to perform one or more operations recited in one or more of Aspects 1-21.

Aspect 25: A computer program product comprising instructions or code for executing one or more operations recited in one or more of Aspects 1-21.

The foregoing disclosure provides illustration and description, but is not intended to be exhaustive or to limit the implementations to the precise form disclosed. Modifications and variations are possible in light of the above disclosure or may be acquired from practice of the implementations.

Some implementations may be described herein in connection with thresholds. As used herein, "satisfying" a threshold may refer to a value being greater than the threshold, more than the threshold, higher than the threshold, greater than or equal to the threshold, less than the threshold, fewer than the threshold, lower than the threshold, less than or equal to the threshold, equal to the threshold, or the like.

As used herein, the term "component" is intended to be broadly construed as hardware, firmware, or a combination of hardware and software. It will be apparent that systems and/or methods, described herein, may be implemented in different forms of hardware, firmware, or a combination of hardware and software. The actual specialized control hardware or software code used to implement these systems and/or methods is not limiting of the implementations. Thus, the operation and behavior of the systems and/or methods were described herein without reference to specific software code—it being understood that software and hardware can be designed to implement the systems and/or methods based on the description herein.

Any of the processing components may be implemented as a central processing unit (CPU) or other processor reading and executing a software program from a non-transitory computer-readable recording medium such as a hard disk or a semiconductor memory device. For example, instructions may be executed by one or more processors, such as one or more CPUs, digital signal processors (DSPs), general-purpose microprocessors, application-specific integrated circuits (ASICs), field programmable logic arrays (FPLAs), programmable logic controller (PLC), or other equivalent integrated or discrete logic circuitry. Accordingly, the term "processor," as used herein refers to any of the foregoing structures or any other structure suitable for implementation of the techniques described herein. Software may be stored on a non-transitory computer-readable medium such that the non-transitory computer readable medium includes a program code or a program algorithm stored thereon which, when executed, causes the processor, via a computer program, to perform the steps of a method.

A controller including hardware may also perform one or more of the techniques of this disclosure. A controller, including one or more processors, may use electrical signals and digital algorithms to perform its receptive, analytic, and control functions, which may further include corrective functions. Such hardware, software, and firmware may be implemented within the same device or within separate devices to support the various techniques described in this disclosure.

A signal processing circuit and/or a signal conditioning circuit may receive one or more signals (e.g., measurement signals) from one or more components in the form of raw measurement data and may derive, from the measurement signal further information. Signal conditioning, as used herein, refers to manipulating an analog signal in such a way that the signal meets the requirements of a next stage for further processing. Signal conditioning may include converting from analog to digital (e.g., via an analog-to-digital converter), amplification, filtering, converting, biasing, range matching, isolation and any other processes required to make a signal suitable for processing after conditioning.

Even though particular combinations of features are recited in the claims and/or disclosed in the specification, these combinations are not intended to limit the disclosure of implementations described herein. Many of these features may be combined in ways not specifically recited in the claims and/or disclosed in the specification. For example, the disclosure includes each dependent claim in a claim set in combination with every other individual claim in that claim set and every combination of multiple claims in that claim set. As used herein, a phrase referring to "at least one of" a list of items refers to any combination of those items, including single members. As an example, "at least one of: a, b, or c" is intended to cover a, b, c, a+b, a+c, b+c, and a+b+c, as well as any combination with multiples of the same element (e.g., a+a, a+a+a, a+a+b, a+a+c, a+b+b, a+c+c, b+b, b+b+b, b+b+c, c+c, and c+c+c, or any other ordering of a, b, and c).

Further, it is to be understood that the disclosure of multiple acts or functions disclosed in the specification or in the claims may not be construed as to be within the specific order. Therefore, the disclosure of multiple acts or functions will not limit these to a particular order unless such acts or functions are not interchangeable for technical reasons. Furthermore, in some implementations, a single act may include or may be broken into multiple sub acts. Such sub acts may be included and part of the disclosure of this single act unless explicitly excluded.

When "a component" or "one or more components" (or another element, such as "a controller" or "one or more controllers") is described or claimed (within a single claim or across multiple claims) as performing multiple operations or being configured to perform multiple operations, this language is intended to broadly cover a variety of architectures and environments. For example, unless explicitly claimed otherwise (e.g., via the use of "first component" and "second component" or other language that differentiates components in the claims), this language is intended to cover a single component performing or being configured to perform all of the operations, a group of components collectively performing or being configured to perform all of the operations, a first component performing or being configured to perform a first operation and a second component performing or being configured to perform a second operation, or any combination of components performing or being configured to perform the operations. For example, when a claim has the form "one or more components configured to: perform X; perform Y; and perform Z," that claim should be interpreted to mean "one or more components configured to perform X; one or more (possibly different) components configured to perform Y; and one or more (also possibly different) components configured to perform Z."

No element, act, or instruction used herein should be construed as critical or essential unless explicitly described as such. Also, as used herein, the articles "a" and "an" are intended to include one or more items and may be used interchangeably with "one or more." Further, as used herein, the article "the" is intended to include one or more items referenced in connection with the article "the" and may be used interchangeably with "the one or more." Where only one item is intended, the phrase "only one," "single," or similar language is used. Also, as used herein, the terms "has," "have," "having," or the like are intended to be open-ended terms that do not limit an element that they modify (e.g., an element "having" A may also have B). Further, the phrase "based on" is intended to mean "based, at least in part, on" unless explicitly stated otherwise. As used herein, the term "multiple" can be replaced with "a plurality of" and vice versa. Also, as used herein, the term "or" is intended to be inclusive when used in a series and may be used interchangeably with "and/or," unless explicitly stated otherwise (e.g., if used in combination with "either" or "only one of").

What is claimed is:

1. A sensor calibration system, comprising:
a first gas concentration sensor configured to measure a thermal conductivity of a target gas, wherein the first gas concentration sensor comprises:
a housing comprising a reference chamber containing a reference gas and a measurement chamber containing a measurement gas,
wherein the reference gas has a first thermal conductivity profile and the measurement gas has a second thermal conductivity profile that is different from the first thermal conductivity profile,
wherein the first thermal conductivity profile and the second thermal conductivity profile are dependent on a first environmental stimulus and a second environmental stimulus,
wherein the reference chamber is a closed chamber containing the reference gas and the measurement chamber is an open chamber exposed to the measurement gas; and
a calibration circuit configured to acquire a first plurality of measurements,
wherein the calibration circuit is configured to acquire the first plurality of measurements while the first environmental stimulus of the reference chamber and the measurement chamber is varied and while the second environmental stimulus of the reference chamber and the measurement chamber is fixed,
wherein each measurement of the first plurality of measurements is representative of a difference in thermal conductivity between a thermal conductivity of the reference gas and a thermal conductivity of the measurement gas,
wherein each measurement of the first plurality of measurements corresponds to a different value of the first environmental stimulus, and
wherein the calibration circuit is configured to determine a first thermal conductivity sensitivity of the first gas concentration sensor based on the first plurality of measurements.

2. The sensor calibration system of claim 1, wherein the first environmental stimulus is temperature and the second environmental stimulus is pressure,
wherein the first environmental stimulus is pressure and the second environmental stimulus is temperature, or
wherein the first environmental stimulus is humidity and the second environmental stimulus is temperature.

3. The sensor calibration system of claim 1, wherein the target gas, the reference gas, and the measurement gas are different gases.

4. The sensor calibration system of claim 3, wherein the target gas is helium gas or hydrogen gas, the reference gas is oxygen gas, nitrogen gas, or air, and the measurement gas is oxygen gas, nitrogen gas, or air.

5. The sensor calibration system of claim 1, wherein the thermal conductivity of the reference gas depends on the first environmental stimulus, the second environmental stimulus, and the first thermal conductivity profile, and
the thermal conductivity of the measurement gas depends on the first environmental stimulus, the second environmental stimulus, and the second thermal conductivity profile.

6. The sensor calibration system of claim 1, wherein the calibration circuit is configured to determine the first thermal conductivity sensitivity of the first gas concentration sensor based on an estimated slope of the first plurality of measurements.

7. The sensor calibration system of claim 6, wherein the first thermal conductivity sensitivity is equal to the estimated slope of the first plurality of measurements.

8. The sensor calibration system of claim 1, wherein, while the measurement chamber is exposed to the target gas and a concentration of the target gas in the measurement chamber is varied, the calibration circuit is configured to acquire a second plurality of measurements,
wherein each measurement of the second plurality of measurements corresponds to a different concentration of the target gas, and
wherein the calibration circuit is configured to determine a first target gas sensitivity of the first gas concentration sensor to the target gas based on the second plurality of measurements.

9. The sensor calibration system of claim 8, wherein the first environmental stimulus of the reference chamber and the measurement chamber is fixed and the second environmental stimulus of the reference chamber and the measurement chamber is fixed while the calibration circuit acquires the second plurality of measurements.

10. The sensor calibration system of claim 8, wherein the calibration circuit is configured to determine the first target gas sensitivity based on an estimated slope of the second plurality of measurements.

11. The sensor calibration system of claim 8, wherein the calibration circuit is configured to calibrate the first gas concentration sensor for performing a measurement of the target gas based on the first target gas sensitivity.

12. The sensor calibration system of claim 8, wherein the first gas concentration sensor is configured to compensate for a measurement of the target gas based on the first target gas sensitivity to generate a compensated measurement of the target gas.

13. The sensor calibration system of claim 8, wherein the calibration circuit is configured to calculate a correction factor based on the first thermal conductivity sensitivity and the first target gas sensitivity,
wherein the calibration circuit is configured to determine a second thermal conductivity sensitivity of a second gas concentration sensor,
wherein the calibration circuit is configured to calculate a second target gas sensitivity of the second gas concentration sensor based on the second thermal conductivity sensitivity and the correction factor, and
wherein the calibration circuit is configured to calibrate the second gas concentration sensor for performing a measurement of the target gas based on the second target gas sensitivity.

14. The sensor calibration system of claim 1, wherein the first gas concentration sensor comprises:

a first reference piezoresistive wire arranged in the reference chamber and exposed to the reference gas, wherein the first reference piezoresistive wire has a first resistance value based on the thermal conductivity of the reference gas; and a first measurement piezoresistive wire arranged in the measurement chamber, and exposed to the measurement gas, and connected to the first reference piezoresistive wire in a first half-bridge, wherein the first measurement piezoresistive wire has a second resistance value based on the thermal conductivity of the measurement gas, wherein, while a voltage is applied across the first half-bridge, the calibration circuit is configured to acquire the first plurality of measurements by sampling an output of the first half-bridge.

15. The sensor calibration system of claim 14, wherein the first gas concentration sensor comprises:

a second reference piezoresistive wire arranged in the reference chamber and exposed to the reference gas, wherein the second reference piezoresistive wire has a third resistance value based on the thermal conductivity of the reference gas; and a second measurement piezoresistive wire arranged in the measurement chamber, and exposed to the measurement gas, and connected to the second reference piezoresistive wire in a second half-bridge, wherein the second measurement piezoresistive wire has a fourth resistance value based on the thermal conductivity of the measurement gas, wherein the first half-bridge and the second half-bridge form a full bridge, and wherein, while the voltage is applied across the full bridge, the calibration circuit is configured to acquire the first plurality of measurements by sampling a differential output of the full bridge.

16. A sensor calibration system, comprising:

a gas concentration sensor configured to measure a thermal conductivity of a target gas, wherein the gas concentration sensor comprises:

a housing comprising a reference chamber containing a reference gas and a measurement chamber containing a measurement gas, wherein the reference gas has a first thermal conductivity profile and the measurement gas has a second thermal conductivity profile that is different from the first thermal conductivity profile, wherein the first thermal conductivity profile and the second thermal conductivity profile are dependent on a first environmental stimulus and a second environmental stimulus, wherein the reference chamber is a closed chamber and the measurement chamber is an open chamber exposed to the measurement gas; and a calibration circuit configured to acquire a first plurality of measurements while the first environmental stimulus of the reference chamber and the measurement chamber is varied and while the second environmental stimulus of the reference chamber and the measurement chamber is fixed, wherein each measurement of the first plurality of measurements is representative of a difference in thermal conductivity between a thermal conductivity of the reference gas and a thermal conductivity of the measurement gas, wherein each measurement of the first plurality of measurements corresponds to a different value of the first environmental stimulus, and wherein the calibration circuit is configured to determine a target gas sensitivity of the gas concentration sensor to the target gas based on the first plurality of measurements.

17. The sensor calibration system of claim 16, wherein the gas concentration sensor is configured to compensate for a measurement of the target gas based on the target gas sensitivity to generate a compensated measurement of the target gas.

* * * * *